United States Patent [19]

Cox et al.

[11] 4,199,584
[45] Apr. 22, 1980

[54] PESTICIDAL ACTIVE FURO[2,3-d] PYRIMIDINE DERIVATIVES, COMPOSITIONS CONTAINING THE SAME AND USE THEREOF

[75] Inventors: John M. Cox, Wokingham; Margaret C. Shephard, Maidenhead, both of England

[73] Assignee: Imperial Chemical Industries Limited, London, England

[21] Appl. No.: 908,456

[22] Filed: May 22, 1978

[30] Foreign Application Priority Data

May 27, 1977 [GB] United Kingdom ............... 22477/77

[51] Int. Cl.² .................... A01N 9/22; A61K 31/505; C07D 491/04
[52] U.S. Cl. ...................................... 424/251; 544/278
[58] Field of Search ......................... 544/278; 424/251

[56] References Cited

U.S. PATENT DOCUMENTS

| | | | |
|---|---|---|---|
| 3,577,420 | 5/1971 | Hess et al. | 544/278 |
| 3,632,763 | 1/1972 | Hess et al. | 544/278 |
| 4,007,187 | 2/1977 | Fauran et al. | 544/278 |

OTHER PUBLICATIONS

Hess et al., "Chemical Abstracts," vol. 72, 1970, col. 31834r.
Marquet et al., "Chemical Abstracts," vol. 72, 1970, col. 78968c.

*Primary Examiner*—Donald G. Daus
*Assistant Examiner*—James H. Turnipseed
*Attorney, Agent, or Firm*—Cushman, Darby & Cushman

[57] ABSTRACT

Furo [2,3-d] pyrimidine derivatives having the formula:

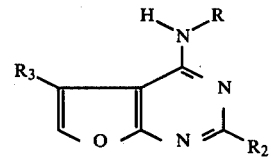

wherein R is alkyl or aralkyl either optionally substituted; $R_2$ is hydrogen or alkyl; $R_3$ is hydrogen or alkyl; and salts thereof; and optical isomers thereof.

3 Claims, No Drawings

PESTICIDAL ACTIVE FURO[2,3-d] PYRIMIDINE DERIVATIVES, COMPOSITIONS CONTAINING THE SAME AND USE THEREOF

This invention relates to furo [2,3-d] pyrimidine derivatives useful as pesticides, to a process for preparing them, to pesticidal compositions containing them, and to a method of combating pesticidal diseases and pests of plants and animals using them.

The invention provides furo [2,3-d] pyrimidine derivatives of the general formula:

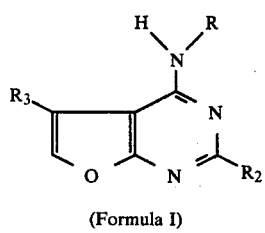

(Formula I)

wherein R is alkyl or aralkyl either optionally substituted; $R_2$ is hydrogen or alkyl; $R_3$ is hydrogen or alkyl; and salts thereof; and optical isomers thereof.

Preferred compounds are those in which R is a straight or branched chain alkyl group especially one containing from 3 to 10 carbon atoms. When R is a substituted alkyl group preferred substituents are alkoxy groups and halogen atoms. Preferred branched chain alkyl groups are alpha-methyl branched alkyl groups. When R is an aralkyl group it is preferably a benzyl group or an alpha-methyl substituted benzyl group, i.e.

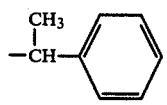

When $R_3$ is an alkyl group it may be, for example, a methyl or ethyl group.

When $R_2$ is an alkyl group it may be, for example, a methyl, ethyl or propyl group.

Specific derivatives according to the invention are listed below in Table I. These correspond to Formula II below, the values for R and $R^3$ being given.

All these specific compounds are novel and fall within the scope of this invention.

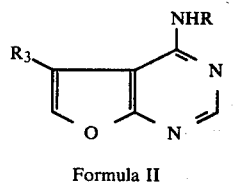

Formula II

TABLE I

| COMPOUND NO | R | M.P. (°C.) | $R^3$ |
|---|---|---|---|
| 1 | $CH(CH_3)_2$ | 156 | $CH_3$ |
| 2 | $CH(CH_3)(CH_2)_4CH_3$ | 79 | $CH_3$ |
| 3 | $CH(CH_3)(CH_2)_2CH_3$ | 120 | $CH_3$ |
| 4 | $(CH_2)_6CH_3$ | 61 | $CH_3$ |
| 5 | $CH(CH_3)C_6H_5$ | b.p. 170° (bath); 0.02 mm | $CH_3$ |
| 6 | $CH(CH_3)(CH_2)_5CH_3$ | 76 | $CH_3$ |
| 7 | $CH(CH_3)C_6H_5$; S-configuration, from (—) amine | b.p. 170° (bath); 0.02 mm | $CH_3$ |
| 8 | $CH(CH_3)(CH_2)_2CH_3$ | 90 | H |
| 9 | $CH(CH_3)(CH_2)_3CH_3$ | — | $CH_3$ |
| 10 | $CH(CH_3)(CH_2)_4CH_3$ | 103–104 | H |
| 11 | $CH(CH_3)(CH_2)_6CH_3$ | — | H |

The furopyrimidine compounds of the invention can be made, for example, either by:

(a) treating an appropriately substituted 2-amino-3-cyanofuran with an orthoester (if necessary in the presence of acetic anhydride), then an amine together with an appropriate base; or (b) treating a furo [2,3-d] pyrimidine containing a labile function (e.g. halo) at the 4-position with an amine or salt thereof.

The derivatives and compositions containing them are active against a wide range of fungal diseases, particularly, for example against:

(a) *Phytophthora infestans* (late blight) on potatoes and tomatoes (b) Powdery mildews, for example:
 *Erysiphe graminis* on cereals
 *Sphaerotheca fuliginea* on cucurbits
 *Podosphaera leucotricha* on apples
 *Uncinula necator* on vines
and other powdery mildews on other hosts (c) Rusts, for example:
 *Puccinia species* on cereals and rusts on, for example, coffee plants, apple trees, vegetables, ornamental plants, and other hosts.

(d) Other fungal diseases, for example:
 *Piricularia oryzae* (blast) on rice
 *Plasmopara viticola* (downy mildew) on vines
 *Venturia inaequalis* (scab) on applies The invention compounds are also variously active against bacterial (nos 1, 2 and 4 of Table I) and viral (nos 3, 6 and 7 of Table I) infections of plants, especially tomato mosaic virus. Some of them also have broad spectrum acaricidal and insecticidal activity including activity against red spider mites (adults and eggs), aphis, californian red scale, flies, caterpillars and beetles. The furo [2,3-d] pyrimidine derivatives, and compositions comprising them, have shown themselves to be particularly useful in combating insect and acarine pests which infest domestic animals, such as *Lucilia sericata*, and ixodid ticks such as Boophilus spp. (e.g. *Boophilus microplus*), Ixodes spp., Amblyomma spp., Rhipicephalus spp., and Dermaceutor spp. They are effective in combating both susceptible and resistant strains of these pests in their adults, larval and intermediate stages of growth, and may be applied to the infested host animal by topical, oral or parenteral administration, using formulations well-known in the art for such purposes.

The invention compounds also display a broad spectrum of anti-fungal and anti-bacterial activity in vitro and are likely to be active against all main groups of these pathogens. Compound No. 1 of Table I is, for example, active against the plant bacterial disease *Xanthomonas oryzae* (rice blight). They also exhibit growth regulating effects on plants.

A particularly valuable feature of the activity of these derivatives is their systemic effect, i.e. their ability to move in a plant to combat an infection or infestation remote from the site of initial application. Thus a derivative, or a composition containing it, may be applied to the soil surrounding the roots of a plant or to the seed or to other plant areas, e.g. leaves, and be taken up by the plant through its roots, or other areas, to combat fungi locally or elsewhere on the plants.

The invention further provides processes for combating pests as described using furo [2,3-d] pyrimidine derivatives, or compositions containing them, as defined above.

The invention also provides pesticidal compositions comprising, as an active ingredient, a furo [2,3-d] pyrimidine derivative as defined above, and a carrier for the active ingredient.

The furo [2,3-d] pyrimidine derivatives and compositions containing them can be used to combat plant fungi and treat plants or seeds in a number of ways, for example they can be applied, formulated or unformulated, directly to the foliage of a plant which is infected or likely to become infected, or they can be applied also to bushes and trees, to soil or to other medium, e.g. rice paddy water, in which plants, bushes or trees are growing or to be planted, or they can be sprayed on, dusted on or applied as a cream or paste formulation. Application can be to any part of the plant, bush or tree, for example to the foliage, stems, branches, seeds or roots, or to soil surrounding the roots.

The term "treating" as used herein refers to all these modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion or emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities; for example by incorporating oils/fats.

The derivatives can be used in smoke generators and also as mixtures with fertilisers (e.g. nitrogen- or phosphorus-containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl alcohol or cetyl alcohol, or with alkyl phenols such as octylphenol, nonylpyenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersion or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, for example other fungicides such as dithiocarbamates, dinocap, dichlofluanid and the like, as well as stabilising agent(s), for example epoxides (e.g. epichlorhydrin).

The invention is illustrated by the following Examples wherein the temperatures are in °C.

EXAMPLE 1

This Example illustrates the preparation of a number of 4-amino-5-methyl-furo [2,3-d] pyrimidines having the structural formula:

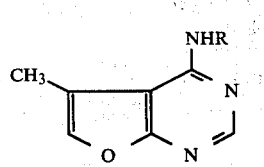

The supposed 2-amino-3-cyano-4-methylfuran (m.p. 156°-8°) described by Gewalt (*Chem. Ber.*, 1966, 99, 1002) has been shown by McKee (*J. Org. Chem.*, 1973, 38, 612) to be the Diels-Alder dimer, 2,4-diamino-3,5-dicyano-3a,6-dimethyl-3a,4,7,7a-tetrahydro-endo-4,7-epoxybenzofuran.

A mixture of malononitrile (17.9 g), triethylamine (14.6 ml) and toluene (140 ml) was stirred at room temperature for ten minutes, then treated with acetol (13.2 g). Following an exothermic reaction, the mixture was refluxed for ten minutes, cooled and the toluene layer decanted. The oily residue was extracted with toluene and the total extracts washed with water, dried and evaporated to give a white solid (7.24 g; m.p. 114°). Recrystallisation from petroleum (b.p. 80°-100°) gave material m.p. 117°, shown to be the unstable monomeric 2-amino-3-cyano-4-methylfuran by analysis and by n.m.r. spectrometry [CDCl$_3$:τ3.43 (1H, singlet); 5.0 (2H, broad); 8.03 (3H, singlet].

A mixture of this freshly prepared material (3.12 g), triethylorthoformate (3.0 ml) and acetic anhydride (0.5 ml) was heated for two and a half hours at 130°, then treated with a mixture of an appropriate primary amine (0.028 mole, approximately 10% excess), acetic acid (5 ml) and anhydrous sodium acetate (3.1 g). The mixture was heated at 130° for a further three hours, cooled, poured into water and extracted with ether. The extracts were washed with water, dried and evaporated and the residue distilled in a bulb-tube apparatus (pressure, ~0.02 mm; bath temperature 130°-170°) to give products as shown in Table II below. In most cases, the distillate solidified and was recrystallised from e.g. petroleum to give material with the melting-point shown. Compound No. 9 was made similarly.

TABLE II

| COMPOUND NO | R | M.P. (°C.) |
|---|---|---|
| 1 | CH(CH$_3$)$_2$ | 156 |
| 2 | CH(CH$_3$)(CH$_2$)$_4$CH$_3$ | 79 |
| 3 | CH(CH$_3$)(CH$_2$)$_2$CH$_3$ | 120 |
| 4 | (CH$_2$)$_6$CH$_3$ | 61 |
| 5 | CH(CH$_3$)C$_6$H$_5$ | b.p. 170° (bath); 0.02 mm |
| 6 | CH(CH$_3$)(CH$_2$)$_5$CH$_3$ | 76 |
| 7 | CH(CH$_3$)C$_6$H$_5$; S-configuration, (−) amine | b.p. 170° (bath); 0.02 mm |

EXAMPLE 2

This Example illustrates the preparation of 4-(2-pentylamino)-furo [2,3-d] pyrimidine having the structural formula:

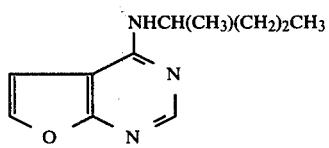

Compound No 8

A mixture of malononitrile (5.85 g), triethylamine (4.8 ml) and toluene (100 ml) was treated with glycolaldehyde (3.75 g, replacing acetol; otherwise as described in Example 1) to give monomeric 2-amino-3-cyanofuran (1.94 g). This freshly prepared material was treated with triethylorthoformate (4.2 ml) and acetic anhydride (0.4 ml), then 2-aminopentane (5.0 ml), acetic acid (3.0 ml) and anhydrous sodium acetate (1.8 g), basically as described in Example 1. The reaction mixture was cooled, diluted with water and extracted with ether. Extraction into 2N hydrochloric acid, followed by basification and reextraction gave the title compound (650 mg; m.p. 90°). Compounds Nos. 10 and 11 were made similarly.

EXAMPLE 3

An emulsifiable concentrate was made up by mixing the ingredients, and stirring the mixture until all the constituents were dissolved.

| | |
|---|---|
| Compound No 1 of Table I | 10% |
| Ethylene dichloride | 40% |
| Calcium dodecylbenzenesulphate | 5% |
| "Lubrol" L | 10% |
| "Aromasol"H | 35% |

EXAMPLE 4

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound No 2 of Table I | 50% |
| "Dispersol" T | 25% |
| "Lubrol" APN 5 | 1.5% |
| Sodium acetate | 23.5% |

EXAMPLE 5

The ingredients were all ground together to produce a powder formulation readily dispersible in liquids.

| | |
|---|---|
| Compound No 3 of Table I | 45% |
| "Dispersol" T | 5% |
| "Lissapol" NX | 0.5% |
| "Cellofas" B600 | 2% |
| Sodium acetate | 47.5% |

EXAMPLE 6

The active ingredient was dissolved in a solvent and the resultant liquid was sprayed on to the granules of China clay. The solvent was then allowed to evaporate to produce a granular composition.

| | |
|---|---|
| Compound No 4 of Table I | 5% |
| China clay granules | 95% |

EXAMPLE 7

A composition suitable for use as a seed dressing was prepared by mixing the three ingredients.

| | |
|---|---|
| Compound No 5 of Table I | 50% |
| Mineral oil | 2% |
| China clay | 48% |

EXAMPLE 8

A dusting powder was prepared by mixing the active ingredient with talc.

| | |
|---|---|
| Compound No 6 of Table I | 5% |
| Talc | 95% |

EXAMPLE 9

A Col formulation was prepared by ball-milling the constituents set out below and then forming an aqueous suspension of the ground mixture with water.

| | |
|---|---|
| Compound No 7 of Table I | 40% |
| "Dispersol" T | 10% |
| "Lubrol" APN5 | 1% |
| Water | |

EXAMPLE 10

A dispersible powder formulation was made by mixing together the ingredients set out below and then grinding the mixture until all were thoroughly mixed.

| | |
|---|---|
| Compound No 8 of Table I | 25% |
| "Aerosol" OT/B | 2% |
| "Dispersol" A.C. | 5% |
| China clay | 28% |
| Silica | 40% |

EXAMPLE 11

This Example illustrates the preparation of a dispersible powder formulation. The ingredients were mixed and the mixture then ground in a comminution mill.

| | |
|---|---|
| Compound No 1 of Table I | 25% |
| "PERMINAL" BX | 1% |
| "Dispersol" T | 5% |
| Polyvinylpyrrolidone | 10% |
| Silica | 25% |
| China clay | 34% |

EXAMPLE 12

The ingredients set out below were formulated into a dispersible powder by mixing and grinding the ingredients.

| | |
|---|---|
| Compound No 2 of Table I | 25% |
| "Aerosol" OT/B | 2% |
| "Dispersol" A | 5% |
| China clay | 68% |

In Examples 3 to 12 the proportions of the ingredients given are by weight.

There now follows an explanation of the compositions or substances represented by the various Trade Marks and Trade Names mentioned above.

LUBROL L: a condensate of nonyl phenol (1 mole) with ethylene oxide (13 moles)

AROMASOL H: a solvent mixture of alkylbenzenes

DISPERSOL T AND AC: a mixture of sodium sulphate and a condensate of formaldehyde with sodium naphthalene sulphonate.

LUBROL APN 5: a condensate of nonyl phenol (1 mole) with naphthalene oxide (5.5 moles).

CELLOFAS B600: a sodium carboxymethyl cellulose thickener.

LISSAPOL NX: A condensate of nonyl phenol (1 mole) with ethylene oxide (8 moles).

AEROSOL OT/B: dioctyl sodium sulphosuccinate.

PERMINAL BX: a sodium alkyl naphthalene sulphonate.

EXAMPLE 13

The furo [2,3-d] pyrimidine derivatives were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the tests conducted, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 9 days according to the disease and environment, as shown in Table III below.

TABLE III

| DISEASE AND PLANT | INTERVAL USUAL TIME (DAYS)* | DISEASE CODE LETTER |
|---|---|---|
| (1) *Puccinia recondita* (wheat) | 8-9 | A |
| (2) *Phytophthora infestans* (tomato) | 3 | B |
| (3) *Plasmopara viticola* (vine) | 6 | C |
| (4) *Piricularia oryzae* (rice) | 6 | D |
| (5) *Botrytis cinerea* (tomatoes) | 5 | E |
| (6) *Erysiphe graminis* | 7 | F |

TABLE III-continued

| DISEASE AND PLANT | INTERVAL USUAL TIME (DAYS)* | DISEASE CODE LETTER |
|---|---|---|
| (barley) | | |

*N.B.
These intervals are not rigid and will vary with the individual tests. Assessment is normally done at the point of optimum disease development commensurate with a practical timetable.

The disease control was recorded by the following grading:
4=No disease
3=0–5%
2=6–25%
1=26–60%
0=>60%

The results are shown in Table IV.

TABLE IV

| COMPOUND NO | DISEASE CODE LETTER | | | | | |
|---|---|---|---|---|---|---|
| | A | B | C | D | E | F |
| 1 | 4 | 3 | 3 | 3 | 0 | 4 |
| 2 | 3 | 4 | 2–3 | — | 0–1 | 3–4 |
| 3 | 2–3 | 4 | 3 | — | 1–3 | 4 |
| 4 | 2–3 | 4 | 3 | 1–2 | 0 | 2–3 |
| 5 | 3 | 4 | 3 | 3 | 0 | 4 |
| 6 | 3 | 4 | 2–3 | 0 | 2 | 4 |
| 7 | 3 | 4 | 3–4 | 3 | 0 | 3 |
| 8 | 3–4 | 4 | 0–1 | 3 | 0 | 3 | number of the pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table V. In this table the first column indicates the name of the pest species. Each of the subsequent columns indicates the host plant or medium on which it was supported, the number of days which were allowed to elapse after the treatment before assessing the mortality of the pests, and the results obtained for each of the compounds numbered as above. The assessment is expressed in integers which range from 0–3.

0 represents less than 30% kill
1 represents 30–49% kill
2 represents 50–90% kill
3 represents over 90% kill A dash (-) in Table V indicates that no test was carried out.

In Table V 'contact test' indicates that both the pests and the medium were treated and 'residual test' indicates that the medium was treated before infestation with the pests.

TABLE V

| PEST SPECIES | SUPPORT MEDIUM | NO. OF DAYS | COMPOUND NO. (TABLE I) | | | | | | |
|---|---|---|---|---|---|---|---|---|---|
| | | | 1 | 2 | 3 | 4 | 5 | 6 | 7 |
| *Tetranychus telarius* (red spider mites, adults) | French Bean | 3 | 0 | 3 | 0 | 3 | 2 | 3 | 0 |
| *Tetranychus telarius* (red, spider mites, eggs) | French Bean | 3 | 0 | 3 | 0 | 3 | 3 | 3 | 3 |
| *Aphis fabae* (black aphids) | Broad Bean | 2 | 0 | 3 | 2 | 3 | 3 | 3 | 3 |
| *Megoura viceae* (green aphids) | Broad Bean | 2 | 0 | 3 | 3 | 3 | 3 | 3 | 3 |
| *Aonidiella aurantii* (California red scale-crawlers) | Potato Tubers | 28 | 3 | 3 | 3 | 3 | 3 | 3 | 3 |
| *Musca domestica* (houseflies - contact test) | Milk/ Sugar | 2 | 0 | 2 | 0 | 1 | 1 | 0 | 0 |
| *Plutella maculipennis* (diamond back moth, larvae) - contact test | Mustard | 13 | 2 | 2 | 2 | 2 | 3 | 0 | 0 |
| *Phaedon cochleariae* (mustard beetles - contact test) | Cabbage | 13 | 0 | 1 | 0 | 2 | 3 | 1 | 0 |

EXAMPLE 14

The activity of a number of the compounds was tested against a variety of insect and other invertebrate pests. The compounds were used in the form of a liquid preparation containing 0.1% by weight of the compound except in the tests with *Aedes aegypti where the preparations contained 0.01% by weight of the compound.* The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

The test procedure adopted with regard to each pest was basically the same and comprised supporting a

EXAMPLE 15

This Example illustrates the ixodicidal activity of the furo [2,3-d] pyrimidine derivatives of the invention against cattle ticks (*Boophilus microplus*).

A suspension of the derivatives of Table I was prepared by ball milling 10 parts of the compound with 985 parts of water and 5 parts of "Teric" N9 ("Teric" is a Registered Trade Mark and "Teric" N9 is a nonionic surfactant obtained by condensing nonylphenol with ethylene oxide in a molar ratio of 1:9) to give a composition containing 1.0% active ingredient. A portion of each of the above suspension was then diluted with water to give compositions containing 0.1% and 0.01% active ingredient.

The efficacy of each of the compounds against engorged adult female ticks of the "Yeerongpilly" strain was tested by applying a microdrop of the appropriate concentration suspension to each of about twenty of the ticks. After 14 days the mortality count of the adult ticks was assessed by counting the eggs laid by them and the percentage of those eggs which had hatched. The results are given in Table VI.

The efficacy of each of the products against larval ticks of the "Yeerongpilly" strain was tested as follows: A sheet of filter paper was soaked in the appropriate concentration suspension and then allowed to dry. The treated paper was converted to the form of an envelope and approximately 100 larval ticks of the "Yeerongpilly" strain were enclosed therein. A mortality count was done on the larval ticks 48 hours after they had been placed in the envelope and the kill rated on a 0-5 scale wherein 0 represents 0-20% kill
1 represents 20-50% kill
2 represents 50-80% kill
3 represents 80-95% kill
4 represents 95-99% kill
5 represents 100% kill The results are given in Table VI.

In a further test an emulsion of each of the products was prepared by mixing 25 parts of the compound with 75 parts of cyclohexanone and 25 parts of "Teric" N9 and diluting the mixture with water to provide 10,000 parts by volume of an emulsion. Each of the emulsions so obtained was sprayed, to drip point, onto calves heavily infested with various stages of the resistant "Viarra" strain of cattle tick. The efficacy of each of the products was assessed as follows:

(i) All adult female ticks which were fully engorged at the time of spraying were collected soon after spraying the calves. They were then placed in a Petri dish in an incubator for assessment of mortality based on capacity to lay eggs, and if eggs were laid, the viability of the eggs as shown by hatch of viable larvae. Engorged adults, if any, were also collected at 24 hours and 48 hours after spraying and the same assessment of mortality was made. This assessment is referred to as "Mortality-Engorged Adults" and the results are given in Table VII.

(ii) At daily intervals predetermined sampling areas on each calf were inspected for the effect of the active ingredient on the immature adults and nymphs. This assessment was rated on the 0-5 scale defined in Example 3 and is referred to as "Mortality-Immature Adults" and "Mortality-Nymphs." The results are given in Table VII. The symbol "-" is used to indicate that no engorged adults were present.

In these tests permethrin (3-phenoxybenzyl (±)-cis/-trans-3(2,2-dichlorovinyl)-2,2-dimethylcyclopropane carboxylate) was used as a standard.

TABLE VI

| | IN VITRO IXODICIDAL ACTIVITY AGAINST ADULTS AND LARVAE | | | | |
|---|---|---|---|---|---|
| | % MORTALITY OF ADULTS | | KILL RATING AGAINST LARVAE | | |
| PRODUCT | 1% a.i. | 0.1% a.i. | 1% a.i. | 0.1% a.i. | 0.01% a.i. |
| 2 | 100 | 70 | 5 | 5 | 5 |
| 4 | 100 | 10 | 5 | 5 | 0 |
| 5 | 80 | 30 | 5 | 5 | 0 |
| 6 | 90 | 10 | 5 | 5 | 5 |
| 8 | 70 | 10 | 5 | 0 | 0 |
| 9 | 70 | 20 | 5 | 5 | 0 |
| 10 | 0 | 20 | 5 | 5 | 0 |

TABLE VII

| | | IN VIVO IXODICIDAL ACTIVITY AGAINST ENGORGED ADULTS, IMMATURE ADULTS AND NYMPHS | | |
|---|---|---|---|---|
| | | MORTALITY | | |
| COMPOUND NO (TABLE I) | % ACTIVE INGREDIENT | ENGORGED ADULTS (%; 24 hr/24 hr/ 48 hr | IMMATURE ADULTS* | NYMPHS* |
| 2 | 0.25 | —/—/— | 5 | 4 |
| 4 | 0.20 | 100/100/100 | 5 | 4 |
| 6 | 0.07 | —/40/— | 4 | 3 |
| 8 | 0.10 | —/0/— | 1 | 0 |

We claim:

1. A process for combating fungi, insects, acarina, and bacteria which infect or infest plants, seeds or animals which comprises applying to plants, seeds, or animals, or to the pests, or to their locus or habitat, or to the soil in which plants or seeds are growing or to be planted an effective amount of a furo [2,3-d] pyrimidine derivative having the formula:

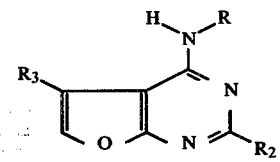

wherein R is an alkoxy- or halo-substituted alkyl having 3 to 10 carbons, an alpha-methyl branched alkyl having 3-10 carbons, a benzyl or alpha-methyl benzyl group; $R_2$ is hydrogen, methyl, ethyl or propyl; $R_3$ is hydrogen, methyl or ethyl, or optical isomers thereof.

2. A process for combating Ixodid ticks comprising applying to the ticks, or to their locus or habitat, or to animals, especially cattle, infested with, or susceptible to infestation with, such ticks, an effective amount of a furo [2,3-d] pyrimidine derivative having the formula:

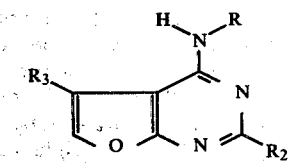

wherein R is an alkoxy- or halo-substituted alkyl having 3 to 10 carbons, an alpha-methyl branched alkyl having 3-10 carbons, a benzyl or alpha-methyl benzyl group; $R_2$ is hydrogen, methyl, ethyl or propyl; $R_3$ is hydrogen, methyl or ethyl, or optical isomers thereof.

3. A process according to claim 2 wherein the ticks are Boophilus species especially *Boophilus microplus*.